United States Patent
Ichikawa (10) Patent No.: US 8,211,021 B2
(45) Date of Patent: Jul. 3, 2012

(54) ULTRASOUND IMAGE PROCESSING APPARATUS AND ULTRASOUND DIAGNOSTIC APPARATUS

(75) Inventor: Junichi Ichikawa, Hino (JP)

(73) Assignee: Olympus Medical Systems Corp., Tokyo (JP)

( * ) Notice: Subject to any disclaimer, the term of this patent is extended or adjusted under 35 U.S.C. 154(b) by 478 days.

(21) Appl. No.: 12/416,413

(22) Filed: Apr. 1, 2009

(65) Prior Publication Data

US 2009/0187105 A1 Jul. 23, 2009

Related U.S. Application Data

(63) Continuation of application No. PCT/JP2006/319769, filed on Oct. 3, 2006.

(51) Int. Cl.
*A61B 8/00* (2006.01)
(52) U.S. Cl. ........ 600/444; 600/446; 600/437; 600/443; 600/440; 382/128
(58) Field of Classification Search .................. 600/437, 600/440, 443, 444, 446, 447; 382/128
See application file for complete search history.

(56) References Cited

U.S. PATENT DOCUMENTS

| | | | | |
|---|---|---|---|---|
| 5,295,485 A | * | 3/1994 | Shinomura et al. | ........... 600/443 |
| 5,680,865 A | * | 10/1997 | Tanaka | ........................ 600/441 |
| 6,717,609 B2 | * | 4/2004 | Sugimoto et al. | ............... 348/74 |
| 7,066,887 B2 | * | 6/2006 | Flesch et al. | ................... 600/447 |
| 7,081,093 B2 | * | 7/2006 | Flesch | ........................... 600/459 |
| 7,204,807 B2 | * | 4/2007 | Tsoref | ............................ 600/438 |
| 2005/0251042 A1 | * | 11/2005 | Sandrin et al. | ................ 600/443 |
| 2008/0103393 A1 | * | 5/2008 | Specht | .......................... 600/437 |
| 2008/0242986 A1 | * | 10/2008 | Ichikawa | ...................... 600/443 |

FOREIGN PATENT DOCUMENTS

| | | |
|---|---|---|
| JP | 03-047240 | 2/1991 |
| JP | 03-165747 | 7/1991 |
| JP | 06-209936 | 8/1994 |
| JP | 10118070 | 5/1998 |
| JP | 2000-300565 | 10/2000 |
| JP | 2004-135693 | 5/2004 |
| JP | 2005-261595 | 9/2005 |
| JP | 2005-279129 | 10/2005 |
| JP | 2006-204560 | 8/2006 |

* cited by examiner

*Primary Examiner* — Brian Casler
*Assistant Examiner* — Amanda Lauritzen
(74) *Attorney, Agent, or Firm* — Scully, Scott, Murphy & Presser, P.C.

(57) ABSTRACT

An ultrasound image processing apparatus includes first and second connecting portions to which first and second ultrasound probes are removably connected, the probes including first and second ultrasound transducers driven by first and second different ultrasound scanning systems respectively. The ultrasound image processing apparatus also includes an ultrasound image signal processing circuit that performs signal processings for generating first and second ultrasound images corresponding to the first and second ultrasound scanning systems from ultrasound signals received by the first and second ultrasound transducers.

15 Claims, 8 Drawing Sheets

ULTRASOUND IMAGE PROCESSING APPARATUS AND ULTRASOUND DIAGNOSTIC APPARATUS

CROSS REFERENCE TO RELATED APPLICATION

This application is a continuation application of PCT/JP2006/319769 filed on Oct. 3, 2006, the entire contents of which are incorporated herein by this reference.

BACKGROUND OF INVENTION

1. Field of the Invention

The present invention relates to an ultrasound image processing apparatus and an ultrasound diagnostic apparatus that perform processing for generating ultrasound images in accordance with different ultrasound scanning systems.

2. Description of the Related Art

A conventional ultrasound diagnostic apparatus applies ultrasound in the shape of pulses to a living body, receives reflected waves of the ultrasound reflected from living tissue to obtain ultrasound tomograms. This apparatus has advantage of noninvasively obtaining diagnostic images of the inside of the living body.

Japanese Patent Application Laid-Open Publication No. 2000-300565 as a first conventional example of such an ultrasound diagnostic apparatus discloses an apparatus that performs mechanical radial scanning for rotating an ultrasound transducer placed in a distal end portion of an ultrasound probe around an axis of the elongated probe and radially scanning ultrasound.

Japanese Patent Application Laid-Open Publication No. 2004-135693 as a second conventional example discloses an apparatus in which an ultrasound transducer array is arranged in a distal end portion of an ultrasound probe substantially in the shape of a protruding surface in an axial direction of the probe and in a cylindrical portion parallel to an axis of the probe, and the ultrasound transducer array is selected to perform electronic convex scanning and radial scanning.

SUMMARY OF THE INVENTION

An ultrasound image processing apparatus according to the present invention includes: first and second connecting portions to which first and second ultrasound probes are removably connected, the probes including first and second ultrasound transducers driven by first and second different ultrasound scanning systems, respectively; and an ultrasound image signal processing portion for performing signal processings for generating first and second ultrasound images corresponding to the first and second ultrasound scanning systems from ultrasound signals received by the first and second ultrasound transducers connected to the first and second connecting portions.

An ultrasound diagnostic apparatus according to the present invention includes: first and second ultrasound probes including first and second ultrasound transducers driven by first and second different ultrasound scanning systems, respectively; first and second connecting portions to which the first and second ultrasound probes are removably connected; and an ultrasound image signal processing portion for performing signal processings for generating first and second ultrasound images corresponding to the first and second ultrasound scanning systems from ultrasound signals received by the first and second ultrasound transducers connected to the first and second connecting portions.

DETAILED DESCRIPTION OF THE PREFERRED EMBODIMENT(S)

Now, embodiments of the present invention will be described with reference to the drawings.

Embodiment 1

Figure 1:
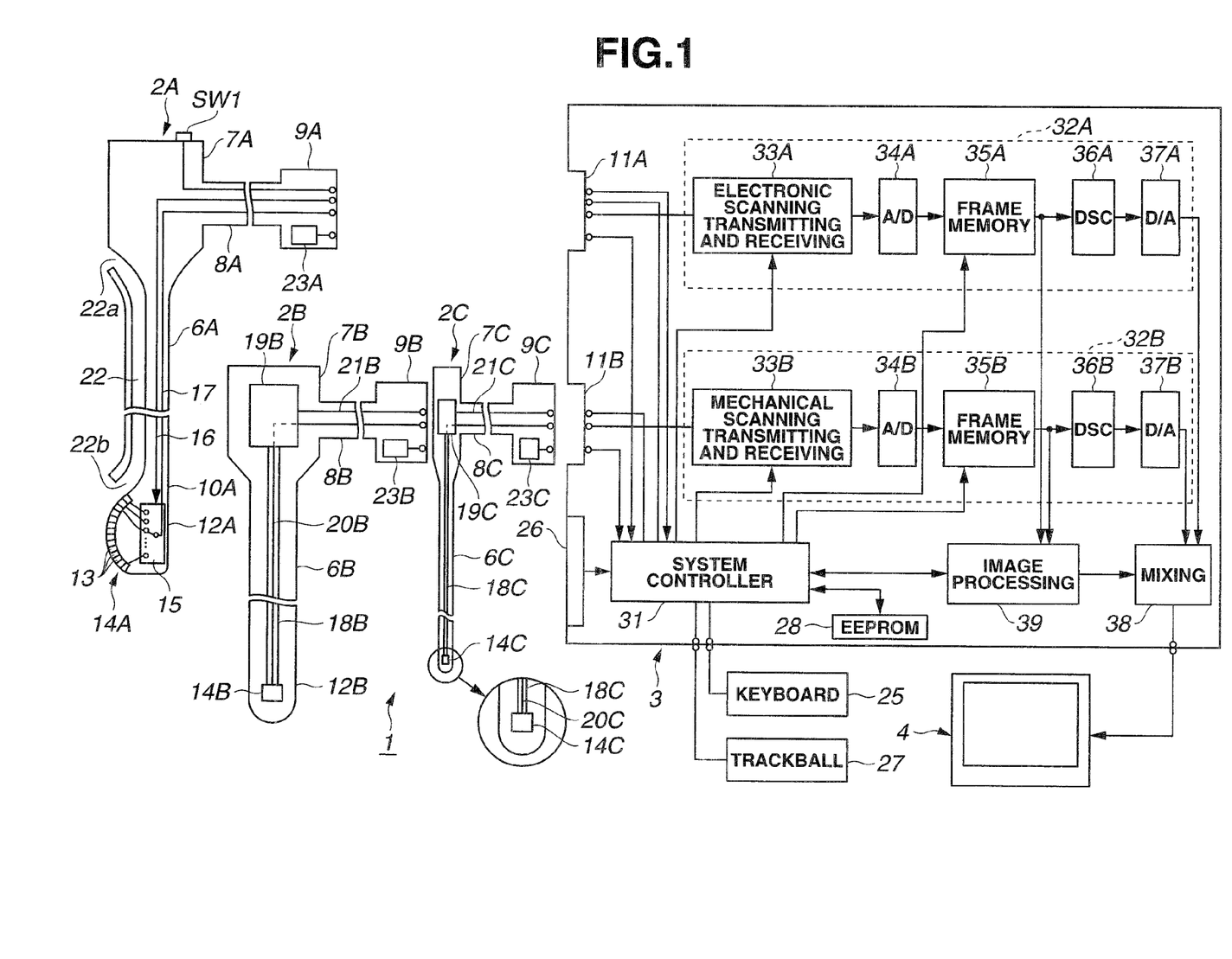
FIG. 1 is a general block diagram of an ultrasound diagnostic system including Embodiment 1 of the present invention.
Figure 2:
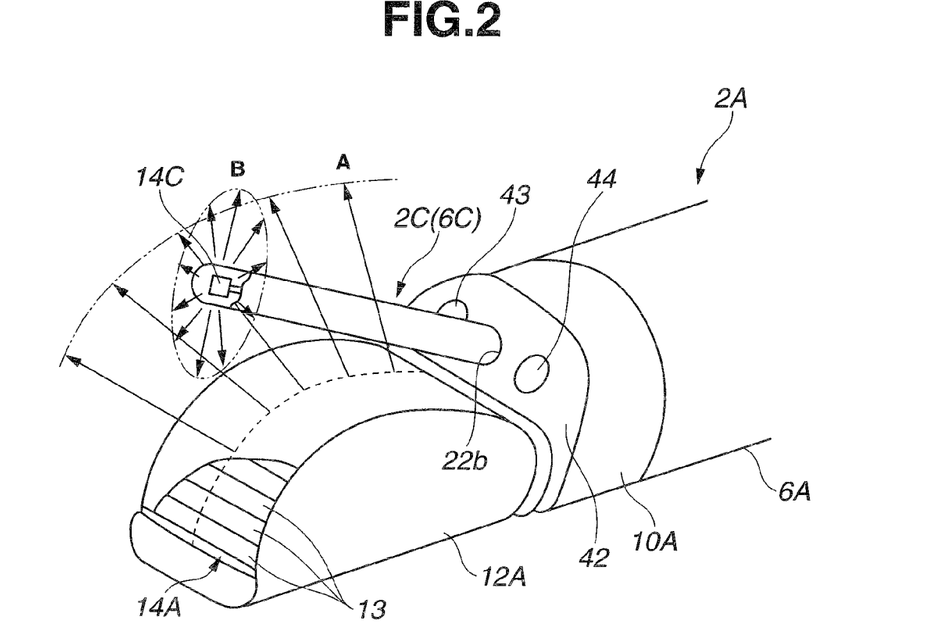
FIG. 2 shows an exemplary use when an ultrasound probe of a mechanical scanning system is inserted through a channel of an ultrasound endoscope of an electronic scanning system, and the ultrasound probe is protruded from a distal end opening of the channel.
Figure 3:
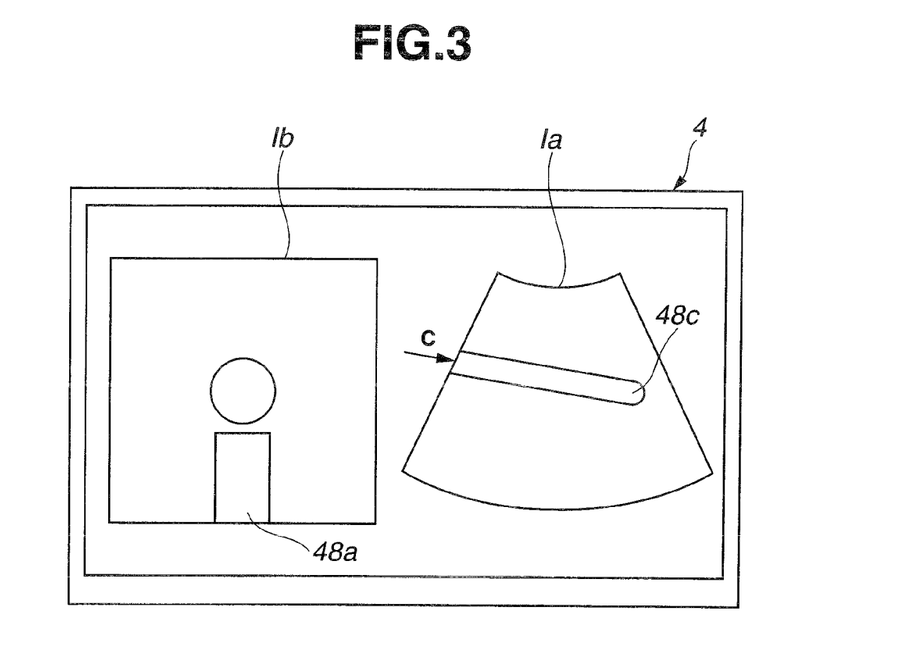
FIG. 3 shows a display example when two ultrasound images are displayed on a monitor.

FIGS. 1 to 4 relate to Embodiment 1 of the present invention, FIG. 1 shows a general configuration of an ultrasound diagnostic system including Embodiment 1 of the present invention, FIG. 2 shows an exemplary use when an ultrasound probe of a mechanical scanning system is inserted through a channel of an ultrasound endoscope of an electronic scanning system, and the ultrasound probe is protruded from a distal end opening of the channel, FIG. 3 shows a display example when two ultrasound images are displayed on a monitor, and FIG. 4 is a timing chart of an operation when two ultrasound transducers are alternately driven. A configuration and an operation of the present embodiment will be described below.

As shown in FIG. 1, an ultrasound diagnostic system 1 including Embodiment 1 of the present invention includes ultrasound endoscopes 2A and 2B of electronic and mechanical scanning systems that are inserted into a body cavity and transmit and receive ultrasound, an ultrasound observation apparatus 3 as an ultrasound image processing apparatus to which the ultrasound endoscopes 2A and 2B can be simultaneously connected, and that drives ultrasound transducers of different scanning systems and generate ultrasound images corresponding to the scanning systems, and a monitor 4 that displays video signals outputted from the ultrasound observation apparatus 3.

The ultrasound diagnostic system 1 may use an ultrasound probe 2C of a mechanical scanning system instead of the ultrasound endoscope 2B of the mechanical scanning system. The ultrasound observation apparatus 3 may include the monitor 4 therein.

The ultrasound endoscopes 2A and 2B have an endoscope function of optical observation as well as an ultrasound probe function of transmitting and receiving ultrasound with ultrasound transducers. For example, as shown in FIG. 2, the ultrasound endoscope 2A includes an illumination window 43 and an observation window 44 in a distal end portion 10A of an insertion portion 6A (the ultrasound endoscope 2B also includes an illumination window and an observation window, though not shown).

For the ultrasound endoscope 2A or 2B, an unshown signal processing apparatus that performs a signal processing of a solid-state image pickup device placed on an image-forming position of an objective lens mounted to the observation window 44, and an unshown monitor to which a video signal outputted from the signal processing apparatus is inputted and that thus displays an endoscope image picked up by the solid-state image pickup device are used.

Inside the illumination window 43, for example, an LED that emits illumination light is placed, and the LED lights and emits illumination light from the illumination window 43 with power supplied from the signal processing apparatus. A light guide may be provided instead of the LED, and transmit illumination light from an external light source device and emit the illumination light from the illumination window 43 to which a distal end of the light guide is mounted.

The ultrasound endoscope 2I (I=A, B) has a grasping portion (or an operation portion) 7I grasped by an operator at a rear end of an elongated insertion portion 6I inserted into the body cavity, and an ultrasound cable 8I is extended from the grasping portion 7I. A connector 9I mounted to an end of the ultrasound cable 8I can be removably connected to a connector receptacle 11I as a connecting portion provided in the ultrasound observation apparatus 3.

The ultrasound endoscope 2A is an ultrasound endoscope of an electronic scanning system. More specifically, the ultrasound endoscope 2A includes an array ultrasound transducer 14A in which a plurality of ultrasound transducer elements 13 are arranged along a protruding surface formed along a longitudinal direction of an insertion portion 6A in a housing 12A provided, for example, at a distal end of the insertion portion 6A, so as to perform convex scanning.

The ultrasound transducer elements 13 are connected to a multiplexer 15 as ultrasound transducer element selecting means provided, for example, in the housing 12A. The ultrasound observation apparatus 3 can apply a selection control signal to the multiplexer 15 via a selecting signal wire 16 to select an ultrasound transducer element 13 that transmits and receives ultrasound via a signal wire 17.

Rear ends of the selecting signal wire 16 used for electronic scanning and the signal wire 17 used for transmitting and receiving ultrasound are connected to contacts of a connector 9A. A user such as an operator can removably connect the connector 9A to an electronic scanning connector receptacle 11A in the ultrasound observation apparatus 3. By this connection, the array ultrasound transducer 14A or the like is connected to a system controller 31 and an electronic scanning transmitting and receiving circuit 33A that constitutes an electronic scanning signal processing portion 32A in the ultrasound observation apparatus 3.

The system controller 31 controls each component in the ultrasound observation apparatus 3, and controls to perform transmitting and receiving corresponding to the ultrasound transducer 14J (J=A to C) included in the ultrasound endoscope 2I or the ultrasound probe 2C connected to the ultrasound observation apparatus 3.

A transmission pulse (driving pulse) outputted from the electronic scanning transmitting and receiving circuit 33A is inputted to the multiplexer 15 as selecting means via the signal wire 17. The multiplexer 15 is driven to successively select the ultrasound transducer elements 13 arranged along the protruding surface of the array ultrasound transducer 14A, and thus the array ultrasound transducer 14A emits ultrasound for electronic convex scanning.

The ultrasound endoscope 2B is an ultrasound endoscope of a mechanical scanning system. More specifically, the ultrasound endoscope 2B includes an ultrasound transducer 14B placed in a housing 12B provided, for example, at a distal end of an insertion portion 6B. The ultrasound transducer 14B is mounted to a distal end of a flexible shaft 18B rotatably inserted along a longitudinal direction of the insertion portion 6B.

A rear end of the flexible shaft 18B is connected to a rotational driving portion 19B provided, for example, in a grasping portion 7B. Rotation of the rotational driving portion 19B is transmitted to the ultrasound transducer 14B via the flexible shaft 18B, and the ultrasound transducer 14B rotates with the rotation of the rotational driving portion 19B.

The ultrasound transducer 14B is inserted, for example, through the flexible shaft 18B, and connected to a distal end of a signal wire 20B used for transmitting and receiving ultrasound. A rear end of the signal wire 20B is connected to a signal wire in an ultrasound cable 8B via an unshown slip ring or the like in the grasping portion 7B, and the signal wire together with a signal wire 21B connected to the rotational driving portion 19B are connected to contacts of a connector 9B.

The connector 9B is connected to a mechanical scanning connector receptacle 11B in the ultrasound observation apparatus 3, and thus connected to the system controller 31 and a mechanical scanning transmitting and receiving circuit (abbreviated as mechanical scanning transmitting and receiving in the drawing) 33B that constitutes a mechanical scanning signal processing portion 32B in the ultrasound observation apparatus 3.

A transmission pulse from the mechanical scanning transmitting and receiving circuit 33B is applied via the signal wire 20B to the ultrasound transducer 14B mechanically rotationally driven. Then, the rotationally driven ultrasound transducer 14B emits ultrasound for (mechanical) radial scanning.

The ultrasound probe 2C includes an insertion portion 6C like the insertion portion 6B of the ultrasound endoscope 2B of the mechanical scanning system with a smaller diameter, a grasping portion 7C provided at a rear end of the insertion portion 6C, and an ultrasound cable 8C extended from the grasping portion 7C. A connector 9C mounted to an end of the ultrasound cable 8C can be removably connected to the mechanical scanning connector receptacle 11B provided in the ultrasound observation apparatus 3.

The ultrasound probe 2C is a miniature probe including the insertion portion 6C that can be inserted through a channel 22 for inserting a treatment instrument provided in the insertion portion 6A of the ultrasound endoscope 2A. The user can insert the insertion portion 6C of the ultrasound probe 2C through an insertion opening 22a of the channel 22 on a side of the grasping portion 7A, and protrude a distal end of the insertion portion 6C forward from a distal end opening 22b.

In a distal end portion of the insertion portion 6c, an ultrasound transducer 14C is placed, which is mounted to a distal end portion of a flexible shaft 18C inserted through the insertion portion 6C. A rear end of the flexible shaft 18C is connected to a rotational driving portion 19C in the grasping portion 7C, and rotation of the rotational driving portion 19C causes rotation of the flexible shaft 18C as well as the ultrasound transducer 14C.

The ultrasound transducer 14C is connected to a signal wire 20C inserted through the flexible shaft 18C and through the ultrasound cable 8C from the grasping portion 7C. A rear end of a signal wire 21C connected to the signal wire 20C and the rotational driving portion 19C is connected to contacts of the connector 9C.

The user connects the connector 9C to the mechanical scanning connector receptacle 11B in the ultrasound observation apparatus 3, and thus as in the ultrasound endoscope 2B, the ultrasound transducer 14C or the like is connected to the system controller 31 and the mechanical scanning transmitting and receiving circuit 33B in the mechanical scanning signal processing portion 32B in the ultrasound observation apparatus 3.

A transmission pulse from the mechanical scanning transmitting and receiving circuit 33B is applied via the signal wire 20C to the ultrasound transducer 14C mechanically rotationally driven. Then, the ultrasound transducer 14C emits ultrasound for radial scanning.

A connector 9J of the ultrasound endoscopes 2A and 2B and the ultrasound probe 2C includes a memory 23J that stores specific identification information of each ultrasound endoscope or ultrasound probe. When the connector 9J is connected to the ultrasound observation apparatus 3, the identification information is read by the system controller 31.

Then, the system controller 31 uses the read identification information to read (identify) whether an ultrasound transducer 14J included in the ultrasound endoscope 2A or 2B or the ultrasound probe 2C is of an electronic scanning system or a mechanical scanning system.

The system controller 31 also reads a type of a scanning system such as convex scanning or radial scanning (or sector scanning) in electronic scanning or mechanical scanning, a scanning range, or the like, and controls to perform ultrasound driving and a signal processing corresponding to the ultrasound transducer 14J included in the connected ultrasound endoscope 2A or 2B or ultrasound probe 2C and the scanning range.

For an ultrasound endoscope or an ultrasound probe including no memory 23J that stores specific identification information in the connector 9J, the ultrasound observation apparatus 3 can accommodate as described below.

The system controller 31 is connected to a keyboard 25 or an operation panel 26. When the above described ultrasound endoscope or ultrasound probe is connected to the ultrasound observation apparatus 3, the user inputs information such as model number or production number of the connected ultrasound endoscope or ultrasound probe from the keyboard 25 or the like.

Instead of the user inputting the information, the information may be previously stored in storing means, for example, an EEPROM provided in the ultrasound endoscope or the ultrasound probe, and the information may be automatically inputted to the system controller 31 when the ultrasound endoscope is connected. In an EEPROM 28, for example, as an electrically rewritable memory as information storing means connected to the system controller 31, information (information on a type of an ultrasound transducer or a scanning system) is stored, from information such as model number or the like, on an ultrasound transducer included in an endoscope or a probe with the model number or the like.

The system controller 31 refers to the information stored in the EEPROM 28, and thus controls the electronic scanning transmitting and receiving circuit 33A, the mechanical scanning transmitting and receiving circuit 33B, or the like so as to perform driving and a signal processing corresponding to the ultrasound transducer included in the ultrasound endoscope or the ultrasound probe.

There is a case, for example, where one connector receptacle 11A has a shape that limits a type of an ultrasound endoscope connectable thereto. In such a case, a type of an ultrasound transducer used is also limited, and thus the system controller 31 may control transmitting and receiving with default setting information corresponding to the case.

For the mechanical scanning system, the system controller 31 controls a rotational driving operation of the rotational driving portion 19B or 19C. For the electronic scanning system, the system controller 31 also controls switching of the multiplexer 15. In the ultrasound endoscope 2A, the multiplexer 15 is included in the ultrasound endoscope 2A, but the multiplexer 15 may be included in the ultrasound observation apparatus 3.

The ultrasound observation apparatus 3 may be adapted to both a type including a multiplexer in an ultrasound endoscope like the ultrasound endoscope 2A and a type including a multiplexer in the ultrasound observation apparatus 3 rather than in the ultrasound endoscope to accommodate both systems. The information in the EEPROM 28 may be updated by a user such as an operator.

As such, in the present embodiment, the ultrasound observation apparatus 3 includes a plurality of connecting portions so that a plurality of ultrasound probes of different ultrasound scanning systems such as the ultrasound endoscope 2I and the ultrasound probe 2C of the electronic scanning system or the mechanical scanning system can be simultaneously connected to the ultrasound observation apparatus 3. When the plurality of ultrasound probes of different scanning systems are simultaneously connected to the ultrasound observation apparatus 3, the ultrasound observation apparatus 3 performs driving and a signal processing corresponding to each scanning system of the plurality of ultrasound probes.

Thus, in the present embodiment, ultrasound examination or ultrasound diagnosis can be performed with, for example, the plurality of ultrasound endoscopes 2A and 2B of different ultrasound scanning systems being connected, without trouble of changing ultrasound observation apparatuses in accordance with an ultrasound endoscope or an ultrasound probe used as in the conventional example.

To the system controller 31, for example, a trackball 27 as a pointing device used in selection instruction or measurement is also connected.

Ultrasound echo signals (corresponding to ultrasound reflection) amplified by unshown receiving amplifiers in the electronic scanning transmitting and receiving circuit 33A and the mechanical scanning transmitting and receiving circuit 33B provided in the ultrasound observation apparatus 3, detected and outputted are converted into digital echo signals by an A/D converter 34I and then stored in a frame memory 35I.

The echo signals stored in the frame memory 35I are read and inputted to a digital scan converter (abbreviated as DSC)

36I, converted into video signals matching a display mode of the monitor 4, and then inputted to a D/A converter 37I. The D/A converter 37I converts the digital video signals into analog video signals and outputs the signals to a mixer 38. The mixer 38 mixes (superimposes) the plurality of inputted video signals and then outputs the signals to the monitor 4.

The echo signals stored in the frame memories 35A and 35B are also inputted to an image processing circuit 39 that performs an image processing. The image processing circuit 39 performs a rotation processing or a scale-down processing of the echo signals stored in the frame memories 35A and 35B to generate a plurality of images, outputs the signals subjected to the image processing to a DSC 36A or 36B, and D/A converts and outputs the signals to the mixer 38.

Thus, the ultrasound observation apparatus 3 that constitutes the ultrasound diagnostic system 1 includes the connector receptacles 11A and 11B as the connecting portions to which the ultrasound endoscopes 2I including the ultrasound transducers 14A and 14B driven by different ultrasound scanning systems are simultaneously removably connected.

The ultrasound observation apparatus 3 can drive the ultrasound transducers 14A and 14B connected to the connector receptacles 11A and 11B by the respective scanning systems and cause the ultrasound transducers 14A and 14B to transmit ultrasound. The ultrasound observation apparatus 3 also includes signal processing means for performing signal processings of ultrasound echo signals obtained from ultrasound reflected from a section with changing acoustic impedance in a site to be examined (diagnosed) in a body cavity into which the insertion portions 6A and 6B are inserted, received by the ultrasound transducers 14A and 14B, and converted into electrical signals.

Video signals generated by the signal processing of the ultrasound echo signals are outputted to the monitor 4 so that ultrasound tomograms by scanning by different scanning systems can be displayed on a display surface of the monitor 4. The video signals can be outputted to the monitor 4 via the mixer 38 to allow ultrasound tomograms generated by different scanning systems to be simultaneously displayed.

For a combination of the ultrasound endoscope 2A and the ultrasound probe 2C with the ultrasound probe 2C being inserted through the channel 22 of the ultrasound endoscope 2A, instead of using the ultrasound endoscope 2B, the ultrasound observation apparatus 3 can perform driving and a signal processing as in the case of the two ultrasound endoscopes 2A and 2B.

FIG. 2 shows an exemplary use when the ultrasound probe 2C is inserted through the channel 22 of the ultrasound endoscope 2A, and the distal end of the ultrasound probe 2C is protruded from the distal end opening 22b of the channel 22.

As shown in FIG. 2, to a distal end portion 10A of the insertion portion 6A of the ultrasound endoscope 2A of the convex electronic scanning system, a proximal end of the housing 12A including the array ultrasound transducer 14A is mounted, and an inclined surface 42 is provided adjacent to the proximal end of the housing 12A.

The plurality of ultrasound transducer elements 13 are arranged along the protruding surface of the housing 12A on a predetermined plane including a longitudinal axis of the insertion portion 6A, and the ultrasound transducer elements 13 arranged on the protruding surface are successively driven to allow convex electronic scanning of ultrasound as shown by the arrow A.

In the inclined surface 42, the illumination window 43 and the observation window 44 for optical endoscope observation are provided, and the distal end opening 22b of the channel 22 is also provided. The user can protrude the distal end of the insertion portion 6C of the ultrasound probe 2C from the distal end opening 22b.

In the distal end portion of the ultrasound probe 2C, an ultrasound transducer 14C is included as shown in FIG. 2, and rotationally driven with a flexible shaft 18C.

Thus, the ultrasound transducer 14C rotationally driven as shown by the arrow B emits ultrasound for radial scanning in a circumferential direction of the insertion portion 6C.

Ultrasound for convex scanning and radial scanning by the ultrasound transducers 14A and 14C, respectively reflected at the section with changing acoustic impedance is again received by the ultrasound transducers 14A and 14C. The ultrasound is then converted into electrical signals by the ultrasound transducers 14A and 14C, inputted to the transmitting and receiving circuits 33A and 33B in FIG. 1, amplified, detected, A/D converted, and temporarily stored in the frame memories 35A and 35B.

Then, the signals are converted into video signals via the DSCs 36A and 36B, and outputted to the monitor 4 as display means for displaying ultrasound images via the mixer 38. Then, as shown in FIG. 3, an ultrasound image Ia by convex scanning and an ultrasound image Ib by radial scanning can be simultaneously displayed adjacent to each other on a display surface of the monitor 4.

In FIG. 3, an image 48c of the distal end of the ultrasound probe 2C is displayed in the ultrasound image Ia by convex scanning, and an image 48a of the distal end of the ultrasound endoscope 2A is displayed in the ultrasound image Ib by radial scanning, corresponding to ultrasound scanning in the state in FIG. 2.

In this case, a position of the distal end opening 22b of the channel 22 of the ultrasound endoscope 2A is fixed, and thus a position of the ultrasound probe 2C in the ultrasound image Ia may be, for example, indicated by a marker as shown by the arrow C. The indication by the marker facilitates understanding correspondence between ultrasound images by different scanning systems. In the ultrasound image Ib, an observation direction of the distal end of the ultrasound endoscope 2A varies depending on circumferential positions of the distal end of the ultrasound probe 2C.

Also in this case, circumferential positioning is performed when the distal end of the ultrasound probe 2C is protruded from the distal end opening 22b, and thus the observation direction of the distal end of the ultrasound endoscope 2A can be determined in the ultrasound image Ib. The direction may be indicated by a marker.

FIG. 4 shows general timing of driving and a signal processing when the ultrasound endoscope 2A and the ultrasound probe 2C are connected to the ultrasound observation apparatus 3, and the user selects a mode for simultaneously displaying the ultrasound images by the two ultrasound transducers 14A and 14C.

When the user selects the mode for simultaneously displaying the ultrasound images by the two ultrasound transducers 14A and 14C, the system controller 31 successively (alternately) drives the two ultrasound transducers 14A and 14C in synchronization with a predetermined signal, for example, as shown in FIG. 4.

Figure 4A:
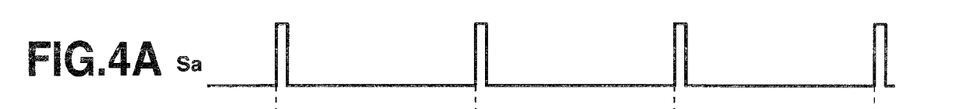
FIGS. 4A to 4F are timing charts of an operation when two ultrasound transducers are alternately driven or an instruction operation to display a still image is performed.
Figure 4B:
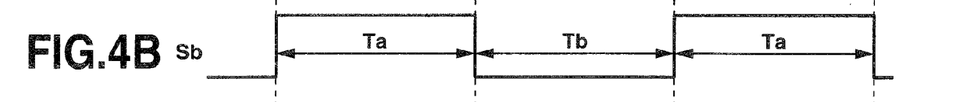

For example, as shown in FIG. 4A, the system controller 31 generates, from a reference signal Sa in generating an image for one frame, a switching signal Sb shown in FIG. 4B in synchronization with the reference signal Sa. Then, the system controller 31 transmits the switching signal Sb to the electronic scanning transmitting and receiving circuit 33A and the mechanical scanning transmitting and receiving circuit 33B.

Figure 4C:
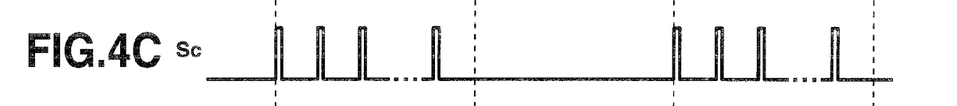

The electronic scanning transmitting and receiving circuit 33A supplies a transmission pulse Sc to the electronic scanning ultrasound transducer 14A in a H level period Ta of the switching signal Sb, as shown in, for example, FIG. 4C, and the ultrasound transducer 14A is ultrasonically excited by application of the transmission pulse Sc and transmits ultrasound.

Figure 4D:
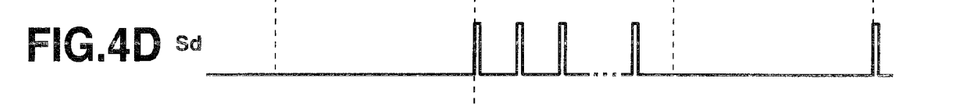

The mechanical scanning transmitting and receiving circuit 33B supplies a transmission pulse Sd to the mechanical radial scanning ultrasound transducer 14B in an L level period Tb of the switching signal Sb as shown in FIG. 4D, and the ultrasound transducer 14B is ultrasonically excited by application of the transmission pulse Sd and transmits ultrasound. The transmission pulses Sc and Sd are actually high frequency pulses with several wavelengths.

For electronic scanning in FIG. 4C, when the transmission pulse Sc is successively supplied to the ultrasound transducer elements 13 at predetermined intervals, a signal for selecting (switching) elements is also outputted to the multiplexer 15 in synchronization with timing of the transmission pulse Sc being outputted.

When each transmission pulse Sc is outputted, an unshown transmitting and receiving changeover switch in the transmitting and receiving circuit 33A is switched so as to select a receiving amplifier side until timing of a next transmission pulse Sc being outputted, and an ultrasound echo signal received by the ultrasound transducer element 13 is inputted to the receiving amplifier.

For mechanical scanning in FIG. 4D, when the transmission pulse Sd is successively applied to the ultrasound transducer 14C at predetermined intervals, a rotational drive signal is supplied to a stepping motor or the like of the rotational driving portion 19C in synchronization with timing of the transmission pulse Sd, and the transmission pulse Sd is successively outputted in synchronization with a rotation angle.

Also in this case, when each transmission pulse Sd is outputted, an unshown transmitting and receiving changeover switch in the transmitting and receiving circuit 33B is switched so as to select a receiving amplifier side until timing of a next transmission pulse Sd being outputted.

As shown in FIGS. 4C and 4D, the two ultrasound transducers 14A and 14C are alternately driven, and thus the transmission pulse of one of the transducers can be prevented from being mixed as noise when the other receives an echo signal in simultaneous driving of the transducers, and ultrasound images can be generated with a high S/N ratio.

When the transmission pulse of one of the transducers can be prevented from being mixed as noise in the echo signal of the other (for example, when ultrasound scanning regions do not overlap), the ultrasound transducers 14A and 14C may be simultaneously driven rather than alternately driven as shown in FIG. 4.

FIGS. 4A to 4D show an example in which the ultrasound transducers 14A and 14C are alternately driven to display ultrasound moving images, but the user may operate a freeze switch SW1 (see FIG. 1) provided, for example, on the grasping portion 7A of the ultrasound endoscope 2A to display the ultrasound image by the ultrasound transducer 14A of the ultrasound endoscope 2A as a still image and the other as a moving image.

Figure 4E:
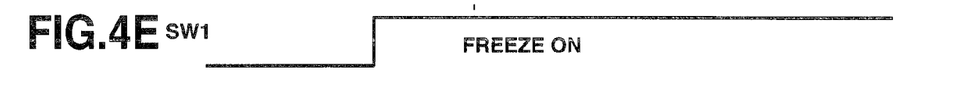
Figure 4F:
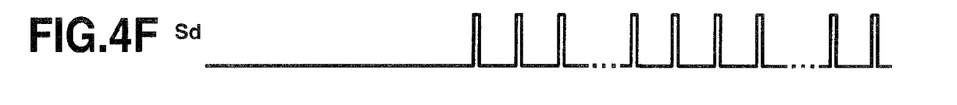

In this case, for example, after a period Tb immediate to timing of operating the freeze switch SW1 as shown in FIG. 4E, ultrasound scanning only by the ultrasound transducer 14C is performed as shown in FIG. 4F, and the ultrasound image by the ultrasound transducer 14C is displayed as a moving image.

After a period Ta immediate to the timing of operating the freeze switch SW1, an update of the ultrasound image obtained by the ultrasound transducer 14A is prohibited, and the ultrasound image is repeatedly displayed as a still image. Specifically, in this state, one displays the still image and the other displays the moving image.

In this case, the ultrasound transducer 14A is actually not used for transmitting and receiving, and thus the ultrasound transducer 14C is used for transmitting and receiving in the entire period including the period Tb and also the period Ta. The system controller 31 performs a control operation in this manner.

When, for example, the user again operates the freeze switch SW1 to cancel a freeze instruction, from the period Ta immediate to timing of the operation, the ultrasound transducers 14A and 14C are again alternately driven to display ultrasound moving images as shown in FIGS. 4C and 4D.

In this example, the freeze switch SW1 is provided on the ultrasound endoscope 2A, but a freeze switch may be also provided on the ultrasound endoscope 2B and the ultrasound probe 2c. An unshown changeover switch may be provided, and the system controller 31 may control to switch between a still image and a moving image when the changeover switch is operated.

An operation by the ultrasound diagnostic apparatus 1 thus configured will be described. The operation by the embodiment will be described for the case where the ultrasound probe 2C is inserted through the channel 22 of the ultrasound endoscope 2A to perform endoscopy or the like as shown in FIG. 2.

The ultrasound endoscope 2A performs convex scanning, and is widely used for inserting a puncture needle through the channel 22 to collect tissue from a site to be diagnosed. In this case, the user can more easily understand a circumferential orientation in the body cavity from an ultrasound image by radial scanning.

Thus, as shown in FIG. 2, the user inserts the ultrasound probe 2C through the channel 22 of the ultrasound endoscope 2A so that ultrasound images by the ultrasound transducers 14A and 14C are displayed. Then, the monitor 4 displays the images Ia and Ib by ultrasound scanning by the ultrasound transducers 14A and 14C as shown in FIG. 3.

As shown in FIG. 3, the ultrasound probe 2C is inserted, and the ultrasound transducer 14C thereof causes the circumferential radical image Ib to be displayed adjacent to and simultaneously with the ultrasound image Ia by convex scanning. Thus, the operator can easily understand the observation orientation by the convex scanning ultrasound transducer 14A in the body cavity by comparing the images Ia and Ib.

When the operator desires to perform, for example, a biopsy after understanding the orientation, the operator can draw the ultrasound probe 2C from the channel 22, insert the puncture needle, puncture a site for the biopsy with a distal end of the needle under observation of the ultrasound image Ia by convex scanning, and collect tissue for the biopsy.

When two channels are provided, tissue can be collected by the puncture needle without drawing the ultrasound probe 2C from the channel 22.

When the biopsy is not performed, ultrasound images that facilitate diagnosis of a site to be examined and therearound can be obtained by the ultrasound transducers 14A and 14C with different scanning directions. Specifically, with one ultrasound image only, information on a direction perpendicular to the scanning direction cannot be obtained, but using the ultrasound transducers 14A and 14C allows an ultrasound image in the direction substantially perpendicular to one scanning direction, and thus the user can easily understand the state of the site to be examined and therearound and thus can easily make a diagnosis.

As such, the ultrasound observation apparatus 3 of the present embodiment can connect the ultrasound probes or ultrasound endoscopes of different scanning systems, drive the different ultrasound transducers included, perform signal processings of received signals, and generate ultrasound images.

Thus, as compared with an ultrasound probe or an ultrasound endoscope of one ultrasound scanning system, the user can easily understand a site of ultrasound scanning and can easily make a diagnosis.

According to the present embodiment, the trouble and operation for changing corresponding ultrasound observation apparatuses for each use of ultrasound endoscopes or ultrasound probes of different scanning systems in the conventional example is saved to significantly increase operability and significantly reduce examination time.

It may be also allowed that general positioning of a site to be examined such as a diseased part is performed by one of two different ultrasound scanning systems, ultrasound scanning is performed in detail by the other system, and detailed ultrasound images are obtained to obtain an ultrasound image that facilitates diagnosis.

Embodiment 2

Figure 5:
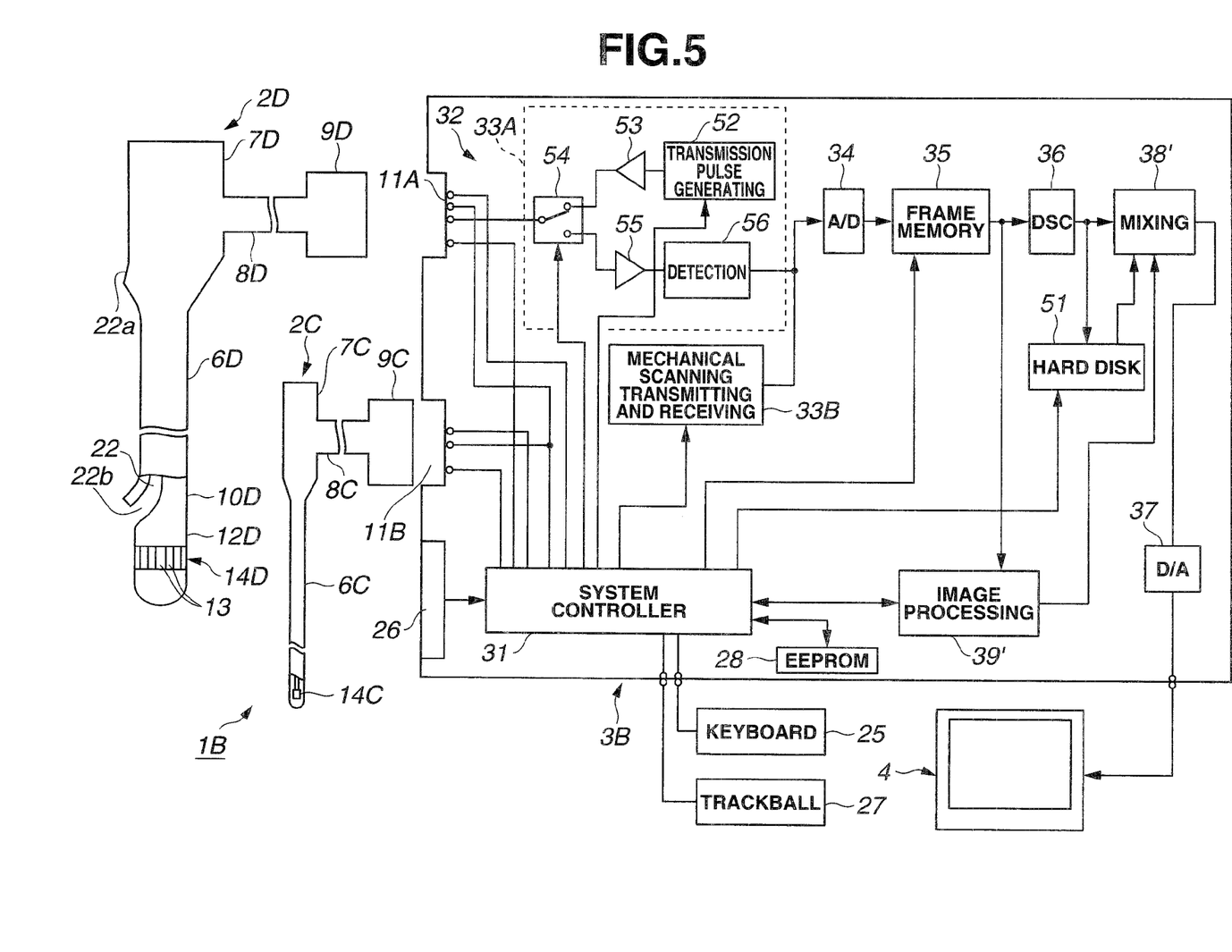
FIG. 5 is a general block diagram of an ultrasound diagnostic system including Embodiment 2 of the present invention.

Next, Embodiment 2 of the present invention will be described with reference to FIGS. 5 to 7. FIG. 5 shows an ultrasound diagnostic system 1B including Embodiment 2 of the present invention. The ultrasound diagnostic system 1B includes an ultrasound endoscope 2D, an ultrasound probe 2C, an ultrasound observation apparatus 3B as an ultrasound image processing apparatus, and a monitor 4.

The ultrasound endoscope 2D includes an array ultrasound transducer 14D in which ultrasound transducer elements 13 are arranged in a circumferential direction of a housing 12D, instead of the convex array ultrasound transducer 14A formed in the housing 12A, in the ultrasound endoscope 2A in FIG. 1. Other configurations of the ultrasound endoscope 2D are the same as those of the ultrasound endoscope 2A, and thus descriptions thereof will be omitted with reference character D being used instead of reference character A in the insertion portion 6A or the like.

The ultrasound endoscope 2D includes a channel 22 through which the ultrasound probe 2C can be inserted.

The ultrasound observation apparatus 3B according to the present embodiment includes a shared signal processing portion 32 in which parts of the electronic scanning signal processing portion 32A and the mechanical scanning signal processing portion 32B in the ultrasound observation apparatus 3 in FIG. 1 are shared. Specifically, an A/D converter 34 to a D/A converter 37 are used that are the A/D converters 34A and 34B to the D/A converters 37A and 37B in FIG. 1 shared. Such sharing realizes an ultrasound image processing apparatus that can accommodate different scanning systems at low cost.

A mixer 38' is herein a digital signal mixer, in which an output signal from a DSC 36 and a digital output signal from an image processing circuit 39' are inputted. Then, the output signal of the mixer 38' is converted into an analog video signal by the D/A converter 37 and outputted to the monitor 4.

The ultrasound observation apparatus 3B according to the present embodiment includes, for example, a hard disk 51 as ultrasound image recording means for recording ultrasound image data outputted from the DSC 36, and can record and read ultrasound image data in and from the hard disk 51 via a system controller 31.

The user can operate, for example, an operation panel 26 to read the ultrasound image data recorded in the hard disk 51, and outputs the data to the monitor 4 via the mixer 38'. For example, when the same site is previously observed and recorded, the ultrasound image data thereof can be read and displayed on the monitor 4 simultaneously with the ultrasound image under observation.

An electronic scanning transmitting and receiving circuit 33A includes a transmission pulse generating circuit 52, a driving amplifier 53 that amplifies a transmission pulse generated by the transmission pulse generating circuit 52 and outputs the transmission pulse to the ultrasound transducer 14D via a changeover switch 54, a receiving amplifier 55 that amplifies an echo signal inputted via the changeover switch 54, and a detection circuit 56 that detects the echo signal amplified by the receiving amplifier 55. A signal detected by the detection circuit 56 is outputted to the A/D converter 34.

The mechanical scanning transmitting and receiving circuit 33B has basically the same block configuration as the electronic scanning transmitting and receiving circuit 33A. In the mechanical scanning transmitting and receiving circuit 33B, a single ultrasound transducer 14C is used for driving and receiving. On the other hand, in the electronic scanning transmitting and receiving circuit 33A, ultrasound transducer elements 13 used for driving and receiving are successively switched.

The electronic scanning transmitting and receiving circuit 33A and other configurations are the same as in Embodiment 1.

Figure 6:
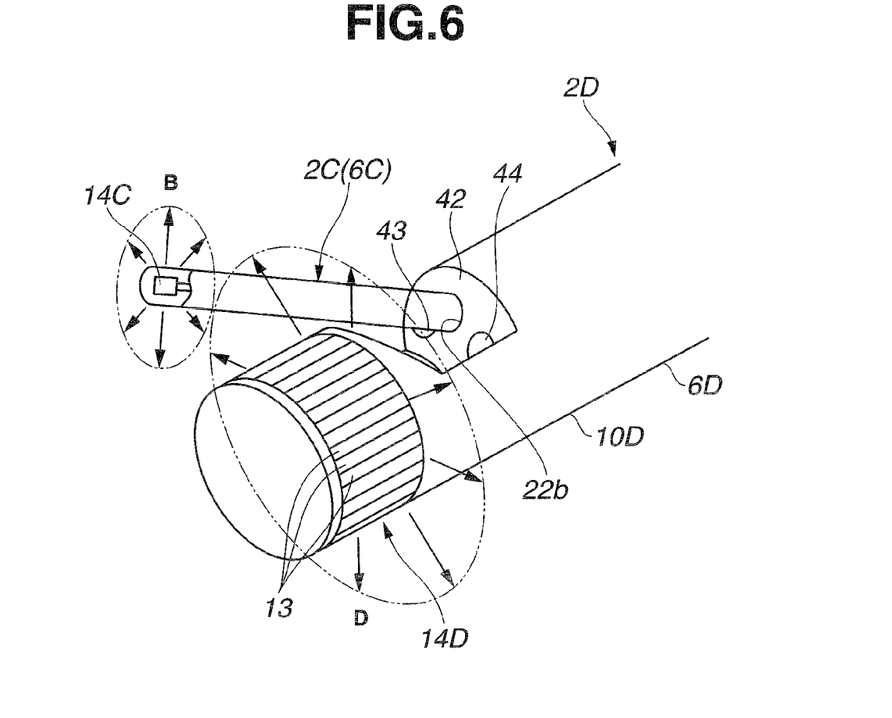
FIG. 6 shows an exemplary use when an ultrasound probe of a mechanical scanning system is inserted through a channel of an ultrasound endoscope of an electronic scanning system, and the ultrasound probe is protruded from a distal end opening of the channel.

A state where the ultrasound probe 2C is inserted through the channel 22 of the ultrasound endoscope 2D in the ultrasound diagnostic system 1B is shown in FIG. 6.

As shown in FIG. 6, a distal end opening 22b of the channel 22 as well as an illumination window 43 and an observation window 44 are provided in an inclined surface 42 formed in a distal end portion 10D, and a distal end of the ultrasound probe 2C is protruded obliquely forward from the distal end opening 22b.

The array ultrasound transducer 14D is provided in which ultrasound transducer elements 13 are arranged along a cylindrical outer circumferential surface of the housing 12D on a front side of the distal end portion 10D. The ultrasound transducer elements 13 are successively driven to emit ultrasound for radial scanning in the direction of the arrow D.

In the present embodiment, the ultrasound transducers 14D and 14C are both for radial scanning, but have different axial directions for radial scanning, and thus information on the different directions can be obtained as compared with an ultrasound image by one of the transducers only. In this case, the ultrasound images displayed on the monitor 4 are as shown in FIG. 7.

Figure 7:
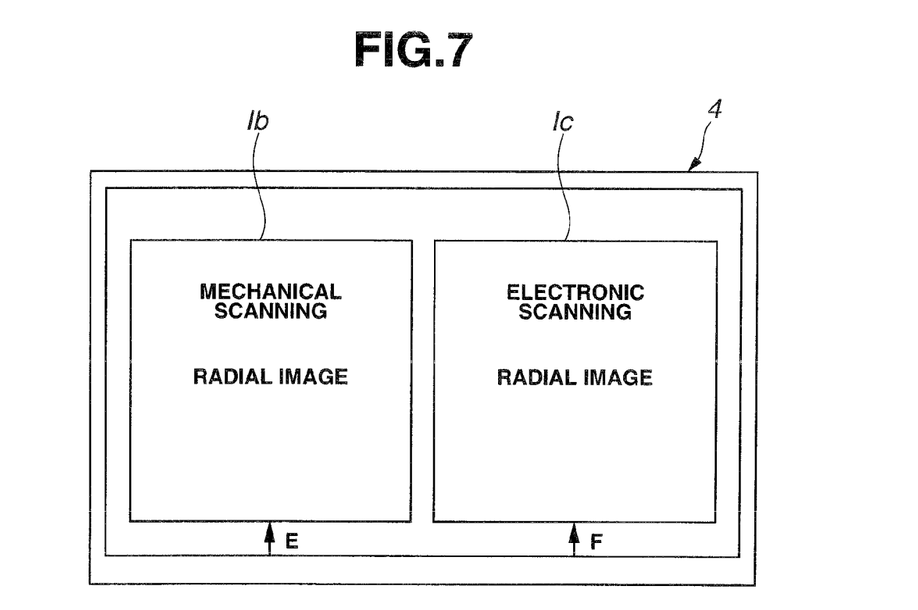
FIG. 7 shows a display example when two ultrasound images are displayed on a monitor.

As shown in FIG. 7, an ultrasound image Ic by electronic radial scanning and an ultrasound image Ib by mechanical radial scanning are simultaneously displayed adjacent to each other. In the ultrasound image Ib, an orientation (circumferential position) of the ultrasound probe 2C is indicated by a marker as denoted by reference character E. When the ultrasound probe 2C inserted through the channel 22 is circumferentially positioned, an observation orientation of the distal end of the insertion portion 6D of the ultrasound endoscope 2D is indicated by a marker as denoted by reference character F in the ultrasound image Ic obtained by the ultrasound transducer 14C of the ultrasound probe 2C.

According to the present embodiment, as in Embodiment 1, the ultrasound images in different directions can be simultaneously obtained, and thus the operator can easily make a diagnosis. Thus, the present embodiment can significantly increase operability for the operator.

Figure 8A:
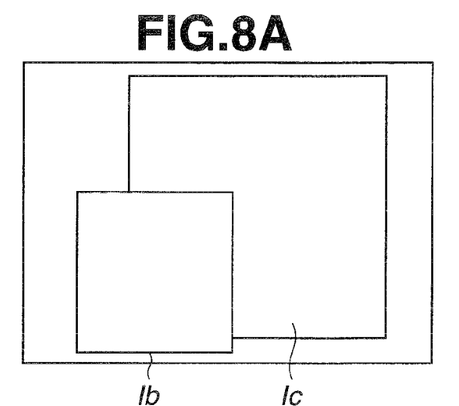
FIG. 8A shows a display example when two ultrasound images are displayed picture-in-picture.

Instead of displaying the ultrasound image Ic by electronic radial scanning and the ultrasound image Ib by mechanical radial scanning in the same size adjacent to each other as shown in FIG. 7, the images may be displayed as master and slave images, that is, picture-in-picture as shown in FIG. 8A.

Figure 8B:
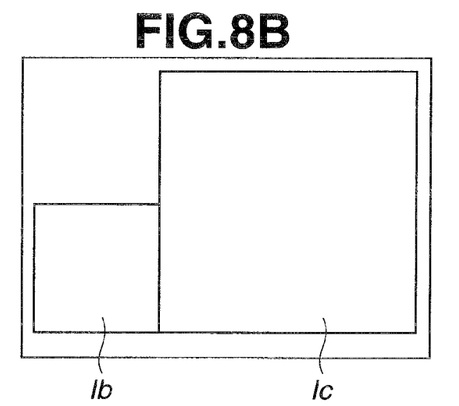
FIG. 8B shows a display example when two ultrasound images are displayed picture-in-picture.

When the images are displayed as master and slave images, the slave image may be displayed to be superimposed on part of the master image as shown in FIG. 8A, or the master image and the slave image may be displayed adjacent to each other as shown in FIG. 8B.

Figure 9:
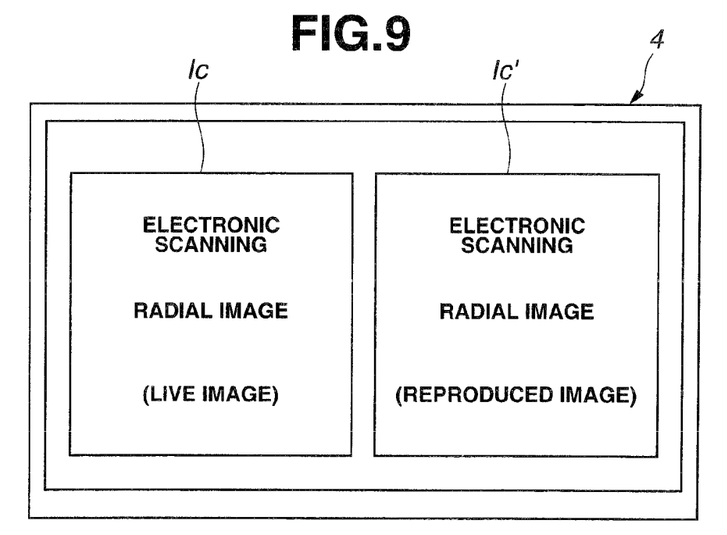
FIG. 9 shows a display example when an ultrasound image read from an image recording apparatus and a live ultrasound image are simultaneously displayed.

Also, as shown in FIG. 9, the radial image Ic by electronic scanning and, for example, a radial image Ic' by electronic scanning recorded in the hard disk 51 in previous ultrasound diagnosis may be simultaneously displayed. Specifically, as shown in FIG. 9, one of the two radial images Ic and Ic' by electronic scanning may be displayed as a live image, and the other as a reproduced image.

Figure 10:
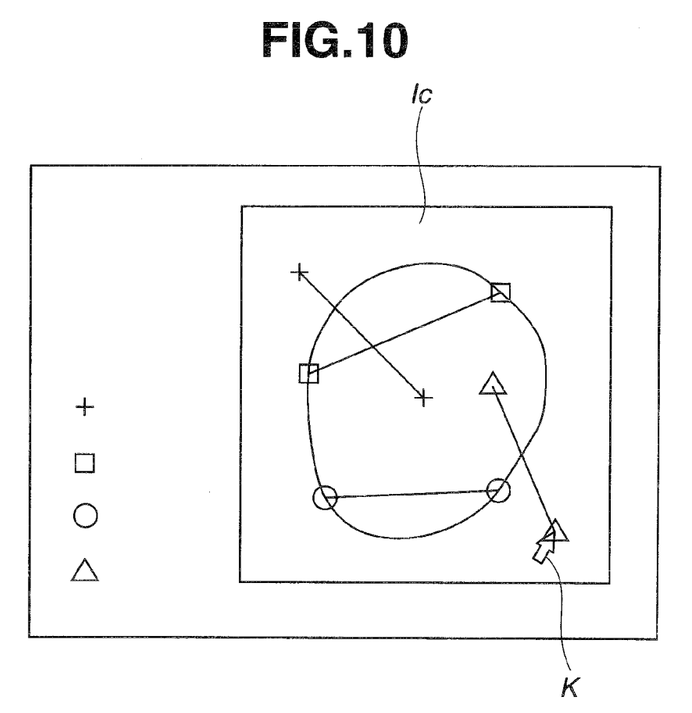
FIG. 10 illustrates an operation in measurement.

In the present embodiment, four-system measuring means is provided. FIG. 10 shows a display example in this case. As shown in FIG. 10, for example, the ultrasound image Ic by electronic radial scanning is displayed as a still image to display a state where distances between two points are measured by four-system marks of, for example, +, □, ○, Δ, and a cursor K used for the measurement can be operated by rotating a trackball 27.

FIG. 10 shows the state of measurement of the distances, but an area or a volume can be measured. The four-system measurement means having a larger number of systems than in a conventional example is used to allow more detail measurement in a short time.

The present embodiment also can accommodate different scanning systems as in Embodiment 1, thereby significantly increasing operability and workability in ultrasound examination or diagnosis, and allowing completion of ultrasound examination in a short time.

Further, a configuration that accommodates mechanical convex scanning or spiral scanning may be allowed. A combination of parts of the above described embodiments or a modified configuration may be allowed. For example, a connector receptacle having a different shape may be provided besides the connector receptacles 11A and 11B to accommodate ultrasound probes and ultrasound endoscopes in a wider range.

Also, for example, a conversion adapter may be connected to the connector receptacle 11A or 11B so as to connect a connector having a shape that cannot be directly connected to the connector receptacle 11A or 11B to accommodate ultrasound probes or ultrasound endoscopes having a connector with a different shape.

Embodiments 1 and 2 have the configuration of the combination of mechanical scanning and electronic scanning, but mechanical scanning may be replaced by electronic scanning.

Figure 11A:
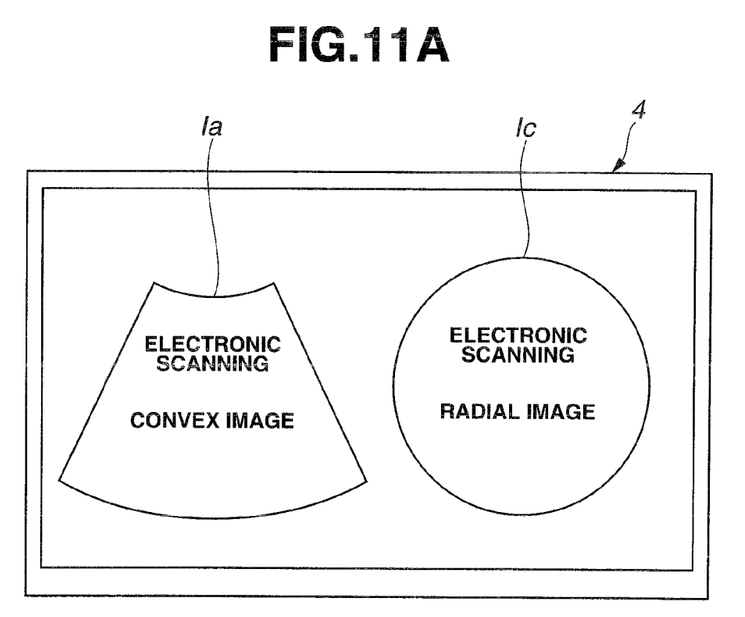
FIG. 11A shows a display example when two ultrasound images are simultaneously displayed in electronic scanning in different directions.

Also, for example, as shown in FIG. 11A, an electronic scanning convex image Ia by the electronic scanning system and an electronic scanning radial image Ic by the electronic scanning system may be simultaneously displayed.

Figure 11B:
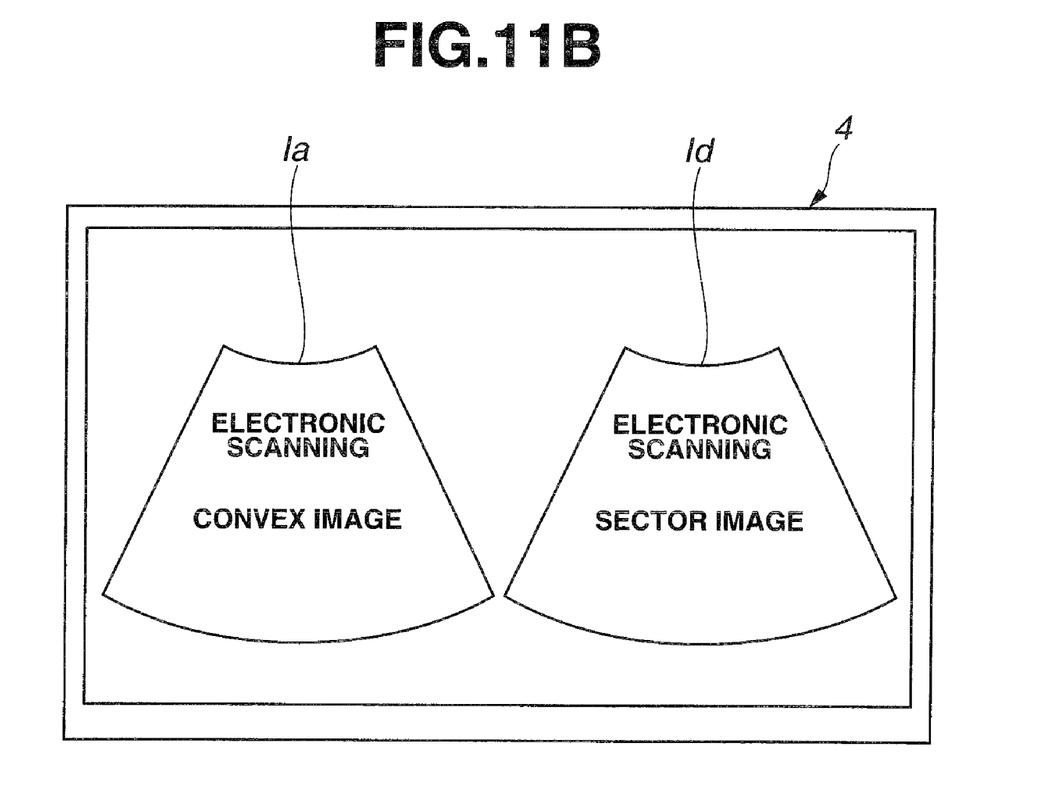
FIG. 11B shows a display example when two ultrasound images are simultaneously displayed in electronic scanning in different directions.

The electronic scanning radial image Ic in FIG. 11A may be replaced by an electronic scanning sector image Id as in FIG. 11B that is a part of the whole circle of the electronic scanning radial image Ic.

FIG. 11B shows a state where the electronic scanning convex image Ia by the electronic scanning system and the electronic scanning sector image Id by the electronic scanning system are simultaneously displayed.

Thus, the plurality of ultrasound images by scanning in the different scanning directions are simultaneously displayed to facilitate understanding and approaching the site to be diagnosed, and facilitate diagnosis and treatment with a treatment instrument. Mechanical sector scanning can be also accommodated for partly scanning in a circumferential direction in mechanical radial scanning.

Embodiments configured by partially combining the above described embodiments also belong to the present invention. Modifications of the above described embodiments also belong the present invention.

What is claimed is:

1. An ultrasound image processing apparatus comprising:
first and second connecting portions to which first and second ultrasound probes are removably connected, the probes including first and second ultrasound transducers driven by first and second different ultrasound scanning systems, respectively;
a transmission portion configured to transmit ultrasound from the first and second ultrasound transducers which are connected to the first and second connecting portions by an electronic scanning system as the first ultrasound scanning system and by a mechanical scanning system as the second ultrasound scanning system, respectively;
an ultrasound image signal processing portion configured to perform signal processing for generating first and second ultrasound images corresponding to the first and second ultrasound scanning systems from ultrasound signals respectively received by the first and second ultrasound transducers;
a control portion configured to perform control of the transmission portion and the ultrasound image signal processing portion and
a freeze switch configured to display a still image;
wherein the control portion is configured to control the transmission portion to alternately perform transmission of the ultrasound by the first and second ultrasound transducers such that a period of transmitting and receiving the ultrasound by the first ultrasound transducer and a period of transmitting and receiving the ultrasound by the second ultrasound transducer do not overlap, and thereby the ultrasound image signal processing portion generates the first and second ultrasound images as moving images, and
the control portion is configured to stop the transmission of the ultrasound from one of the first and second ultrasound transducers in response to an operation of the freeze switch, and to perform the control such that the ultrasound image by the one of the first and second ultrasound transducers is displayed as a still image which corresponds to the stop of the transmission of the ultrasound and such that the ultrasound image by the other of the first and second ultrasound transducers is displayed as a moving image by transmitting and receiving the ultrasound only from the other of the first and second ultrasound transducers in an entire period of transmitting and receiving the ultrasound.

2. The ultrasound image processing apparatus according to claim 1, wherein the ultrasound image signal processing portion is configured to generate simultaneous display video signals for simultaneously displaying the first and second ultrasound images on a display portion.

3. The ultrasound image processing apparatus according to claim 1, further comprising a display portion configured to display the first and second ultrasound images, wherein the display portion is configured to simultaneously display the first and second ultrasound images as moving images.

4. The ultrasound image processing apparatus according to claim 1, further comprising a display portion configured to display the first and second ultrasound images, wherein the display portion is configured to simultaneously display one of the first and second ultrasound images as a moving image and the other as a still image.

5. The ultrasound image processing apparatus according to claim 4, further comprising a switching instruction portion configured to switch display of the moving image and the still image.

6. The ultrasound image processing apparatus according to claim 4, further comprising an ultrasound image recording portion configured to record the first or second ultrasound image.

7. The ultrasound image processing apparatus according to claim 6, wherein the display portion is configured to display the first or second ultrasound image recorded in the ultrasound image recording portion.

8. The ultrasound image processing apparatus according to claim 1, further comprising an information reading portion configured to read, from an ultrasound probe actually connected to at least one of the first and second connecting portions, information on the scanning system of the ultrasound transducer included in the ultrasound probe.

9. The ultrasound image processing apparatus according to claim 8, wherein the control portion is configured to refer to the information and controlling driving and a signal processing corresponding to the scanning system of the ultrasound transducer included in the ultrasound probe.

10. An ultrasound diagnostic apparatus comprising:
first and second ultrasound probes including first and second ultrasound transducers driven by first and second different ultrasound scanning systems, respectively;
first and second connecting portions to which the first and second ultrasound probes are removably connected;
a transmission portion configured to transmit ultrasound from the first and second ultrasound transducers which are connected to the first and second connecting portions by an electronic scanning system as the first ultrasound scanning system and by a mechanical scanning system as the second ultrasound scanning system, respectively;
an ultrasound image signal processing portion configured to perform signal processing for generating first and second ultrasound images corresponding to the first and second ultrasound scanning systems from ultrasound signals respectively received by the first and second ultrasound transducers;
a control portion configured to perform control of the transmission portion and the ultrasound image signal processing portion; and
a freeze switch to display a still image;
wherein the control portion is configured to control the transmission portion to alternately perform transmission of the ultrasound by the first and second ultrasound transducers such that a period of transmitting and receiving the ultrasound by the first ultrasound transducer and a period of transmitting and receiving the ultrasound by the second ultrasound transducer do not overlap, and thereby the ultrasound image signal processing portion generates the first and second ultrasound images as moving images, and the control portion is configured to stop the transmission of the ultrasound from one of the first and second ultrasound transducers in response to an operation of the freeze switch, and to perform the control such that the ultrasound image by the one of the first and second ultrasound transducers is displayed as a still image which corresponds to the stop of the transmission of the ultrasound and such that the ultrasound image by the other of the first and second ultrasound transducers is displayed as a moving image by transmitting and receiving the ultrasound only from the other of the first and second ultrasound transducers in an entire period of transmitting and receiving the ultrasound.

11. The ultrasound diagnostic apparatus according to claim 10, wherein the first or second ultrasound transducer of the electronic scanning system is configured for sector scanning or radial scanning for scanning ultrasound in a circumferential direction of the first or second ultrasound probe, or convex scanning for scanning in the shape of a protruding surface on a plane including a longitudinal direction of the first or second ultrasound probe.

12. The ultrasound diagnostic apparatus according to claim 10, wherein the first or second ultrasound transducer of the mechanical scanning system is configured for sector scanning or radial scanning for scanning ultrasound in a circumferential direction of the first or second ultrasound probe, or convex scanning for scanning in the shape of a protruding surface on a plane including a longitudinal direction of the first or second ultrasound probe.

13. The ultrasound diagnostic apparatus according to claim 10, further comprising an information reading portion configured to read, from an ultrasound probe actually connected to at least one of the first and second connecting portions, information on the scanning system of the ultrasound transducer included in the ultrasound probe.

14. The ultrasound diagnostic apparatus according to claim 13, wherein the control portion is configured to refer the information and controlling driving and a signal processing corresponding to the scanning system of the ultrasound transducer included in the ultrasound probe connected.

15. The ultrasound diagnostic apparatus according to claim 10, further comprising a marker display portion configured to indicate correspondence between the first and second ultrasound images displayed by different ultrasound scanning systems.

* * * * *